(12) United States Patent
Kaiser et al.

(10) Patent No.: US 8,773,649 B2
(45) Date of Patent: Jul. 8, 2014

(54) DEVICE FOR CLAMPING A HOSE LINE FOR DETERMINING THE CONCENTRATION OF A BLOOD CONSTITUENT

(71) Applicants: Martin Kaiser, Hassfurt (DE); Reinhard Koehler, Helmbrechts (DE); Wei Zhang, Niederwerrn (DE); Carsten Mueller, Euerbach (DE)

(72) Inventors: Martin Kaiser, Hassfurt (DE); Reinhard Koehler, Helmbrechts (DE); Wei Zhang, Niederwerrn (DE); Carsten Mueller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 88 days.

(21) Appl. No.: 13/645,801

(22) Filed: Oct. 5, 2012

(65) Prior Publication Data

US 2013/0090540 A1   Apr. 11, 2013

Related U.S. Application Data

(60) Provisional application No. 61/543,837, filed on Oct. 6, 2011.

(30) Foreign Application Priority Data

Oct. 6, 2011   (DE) .......................... 10 2011 114 930

(51) Int. Cl.
    *G01N 33/48*   (2006.01)
    *G01N 1/10*   (2006.01)
(52) U.S. Cl.
    USPC ............................................ 356/39; 356/246
(58) Field of Classification Search
    USPC .................................................... 356/39, 246
    See application file for complete search history.

(56) References Cited

U.S. PATENT DOCUMENTS 5,372,136 A    12/1994   Steuer et al.
7,420,658 B2 *  9/2008   Petterson et al. ............... 356/39

FOREIGN PATENT DOCUMENTS

| DE | 19530969 A1 | 2/1997 |
| EP | 1 579 196 B1 | 9/2005 |
| WO | 2004/057313 | 7/2004 |
| WO | 2008/000433 A1 | 1/2008 |

OTHER PUBLICATIONS

PCT International Search Report from PCT/EP2012/004099, mailed on Apr. 22, 2013.

* cited by examiner

*Primary Examiner* — Roy M Punnoose
(74) *Attorney, Agent, or Firm* — Kenyon and Kenyon LLP

(57) ABSTRACT

A device for clamping a hose line for determining the concentration of a constituent of blood in a hose line, in particular in the hose line of an extracorporeal blood circuit of an extracorporeal blood treatment apparatus, includes a clamping unit with two receiving elements and an electric motor-driven actuation mechanism. Actuation mechanism is constituted such that, when a clamping force is applied, the first and second receiving element can be moved from a position releasing the hose line into a position clamping the hose line. Moreover, the device comprises an unlocking mechanism which is constituted such that, by actuating an unlocking element, the actuation mechanism in the position clamping the hose line can be decoupled from electromotive drive. Unlocking mechanism makes it possible for the receiving elements to be transferred easily and rapidly by hand from the position clamping the hose line into the position releasing the hose line.

15 Claims, 4 Drawing Sheets

DEVICE FOR CLAMPING A HOSE LINE FOR DETERMINING THE CONCENTRATION OF A BLOOD CONSTITUENT

CROSS REFERENCE TO RELATED APPLICATIONS

The present application claims priority to U.S. Provisional Application Ser. No. 61/543,837, filed on Oct. 6, 2011, and claims priority to Application No. DE 10 2011 114 930.2, filed in the Federal Republic of Germany on Oct. 6, 2011, each of which is expressly incorporated herein in its entirety by reference thereto.

FIELD OF INVENTION

The present invention relates to a device for clamping a hose line for determining the concentration of a constituent of blood in a hose line, in particular in the hose line of an extracorporeal blood circuit of an extracorporeal blood treatment apparatus, which comprises a clamping unit for the hose line and a measurement unit for coupling electromagnetic radiation into the blood and measuring the electromagnetic radiation emerging from the blood.

BACKGROUND INFORMATION

Various methods are known for determining the concentration of specific constituents in a patient's blood. Methods for measuring the concentration of blood constituents which require a blood sample to be taken are known in the prior art. Measurement methods are however also known, in which the concentration of blood constituents is measured while the blood is flowing through the hose line. These methods are used especially when the blood is flowing in the hose line of an extracorporeal blood circuit in an extracorporeal blood treatment.

International Patent Publication No. WO 2008/000433 describes a device for determining the concentration of specific blood constituents in a blood-filled, essentially transparent hose line of an extracorporeal blood circuit. The known device makes it possible in particular to determine the haemoglobin concentration and the fraction of red blood corpuscles (erythrocytes) in the total volume of the blood. During the measurement, the hose line is clamped between two parallel, plane contact faces, so that the hose is deformed at the sides lying opposite one another. With a light emitter, light of a specific wavelength is coupled through the transparent hose line into the blood, whilst the scattered or transmitted light is measured with a light detector. The haematocrit is then determined from the ratio of the intensity of the light entering into the blood and emerging from the blood.

European Patent No. EP 1 579 196 B1 describes a device for determining blood constituents, which comprises a clamping unit for clamping the hose line and a measurement unit. The clamping unit is constituted such that the clamped hose line has a square cross-section. The measurement unit comprises a plurality of light emitters and light detectors which are disposed around the periphery of the hose line. The light emitters and light detectors are disposed in such a way that the light emitters lie in a different plane from the light detectors, so that light emitters and light detectors do not lie opposite one another. For the measurement of the blood parameters, the hose line is deformed in the clamping unit. It must be ensured that the hose line does not get jammed in the clamping unit.

SUMMARY

The determination of the blood parameters should be able to be carried out by the user with a high degree of precision and at low cost. A precise determination of the blood parameters requires reproducible clamping of the hose line under predetermined conditions. The cost of the measurements can be reduced if the measuring procedure is automated.

An object underlying the present invention is to provide a device for clamping a hose line for determining the concentration of blood constituents in a hose line, which permits an automatic measuring procedure with a highly degree of measurement accuracy.

The device according to the present invention for clamping a hose line comprises a clamping unit with two receiving elements and an electric motor-driven actuation mechanism. The actuation mechanism is constituted such that, when a clamping force is applied, the first and second receiving element can be brought out of a position releasing the hose line into a position clamping the hose line. With the electric motor-driven actuation mechanism, it is possible not only to automate the clamping of the hose line, but a reproducible measurement of the blood parameters can also be achieved.

Moreover, the device according to the present invention comprises an unlocking mechanism, which is constituted such that, by actuating an unlocking element, the actuation mechanism in the position clamping the hose line can be decoupled from the electromotive drive. The unlocking mechanism makes it possible for the receiving elements of the clamping unit to be transferred easily and rapidly by hand from the position clamping the hose line into the position in which the receiving elements release the hose line. The receiving elements can thus be opened at any time even in the case of failure of the electromotive drive.

In a preferred exemplary embodiment, the actuation mechanism comprises a toggle system, with which the clamping procedure of the hose line can be carried out by applying a predetermined clamping force. With the toggle system, a relatively large clamping force can be applied to the hose line with a relatively small travel path of the receiving elements.

In a further preferred exemplary embodiment, the unlocking element of the unlocking mechanism in the locked position connects a driver of a spindle drive to an actuation element of the toggle system, so that the driver drives the actuation element. In the unlocked position, the driver releases the actuation element. When the driver releases the actuation element, the actuation element can be displaced manually from the position clamping the hose line into the position in which the receiving elements release the hose line.

The electromotive spindle drive permits the application of a relatively large reproducible clamping force on the hose line with the assistance of the toggle system, with a relatively small motor power. The toggle system preferably comprises two cooperating toggles which are actuated by the actuation element of the actuation mechanism.

A further particularly preferred exemplary embodiment makes provision such that the driver is an essentially hollow-cylindrical body with an internal thread, which sits on the spindle of the spindle drive, whilst the actuation element is an essentially hollow-cylindrical body which sits on the hollow-cylindrical body of the driver in a longitudinally displaceable manner. With this particularly preferred exemplary embodiment, the hollow-cylindrical body of the actuation element or driver preferably comprises recesses or grooves running normal to the longitudinal axis. The unlocking element preferably comprises a locking pin, which in the locked position engages in the recesses or grooves of the actuation element or driver, so that the actuation element and the driver are connected to one another. The unlocking element is preferably swivellable, so that the driver and the actuation element can be engaged or disengaged by swivelling the unlocking element.

In a preferred exemplary embodiment, the actuation mechanism comprises at least one pair of lever arms, wherein the first receiving element is fixed to the one end piece of a lever arm and the second receiving element is fixed to the end piece of the other lever arm. The other end pieces of the lever arms are each mounted in a rotational manner at a bearing point. At least one of the two bearing points, at which the other end pieces of the lever arms are mounted in a rotational manner, is preferably constituted such that the end piece of the lever arm can be displaced between two stops. The end piece of the lever arm is pre-tensioned in a spring-loaded manner in the direction of a stop.

The actuation mechanism with the two lever arms permits a reproducible application of a predetermined pre-tensioning force independent of manufacturing tolerances and other influences, for example temperature changes or ageing of materials, which can have an effect on the actuation mechanism. A defined clamping force is exerted with the spring-loaded pre-tensioning. In a particularly preferred exemplary embodiment, at least one pressure spring, which is disposed between the two lever arms, is provided for the application of the spring-loaded pre-tensioning.

A uniform application of the pre-tensioning force over the whole length or width of the receiving elements is preferably achieved by the fact that a first pair of lever arms and a second pair of lever arms are provided, wherein the first pair of lever arms is disposed on the one side of the receiving elements, in particular on their end faces, and the second pair of lever arms is disposed on the other side of the lever elements, in particular on their end faces.

Twisting or jamming of the hose line is preferably avoided by the fact that the receiving elements are mounted in a pendulum-like manner on the lever arms. The pendulum-like motion is preferably limited by stops, so that the receiving elements can only be slightly tilted.

Moreover, the receiving elements are held by guide elements in a defined position preferably during clamping of the hose line. The guide elements comprise guide faces engaging with the receiving elements, said guide faces being orientated in such a way that the receiving elements move towards one another or away from one another on an axis without thereby becoming slanted or misaligned.

A further particularly preferred exemplary embodiment makes provision such that the first receiving element comprises two plane contact faces at right angles to one another and the second receiving element comprises two plane contact faces at right angles to one another, wherein the first and second receiving element can be moved towards one another on an axis which makes an angle of 45° with the plane contact faces of the first and second receiving elements. It is unimportant how the two receiving elements are constituted, as long as the plane contact faces at right angles to one another are present. The receiving elements with the plane contact faces deform the hose line when the clamping unit is closed.

Exemplary embodiments of the present invention are explained below in greater detail with reference to the accompanying drawings.

DETAILED DESCRIPTION

Figure 1:
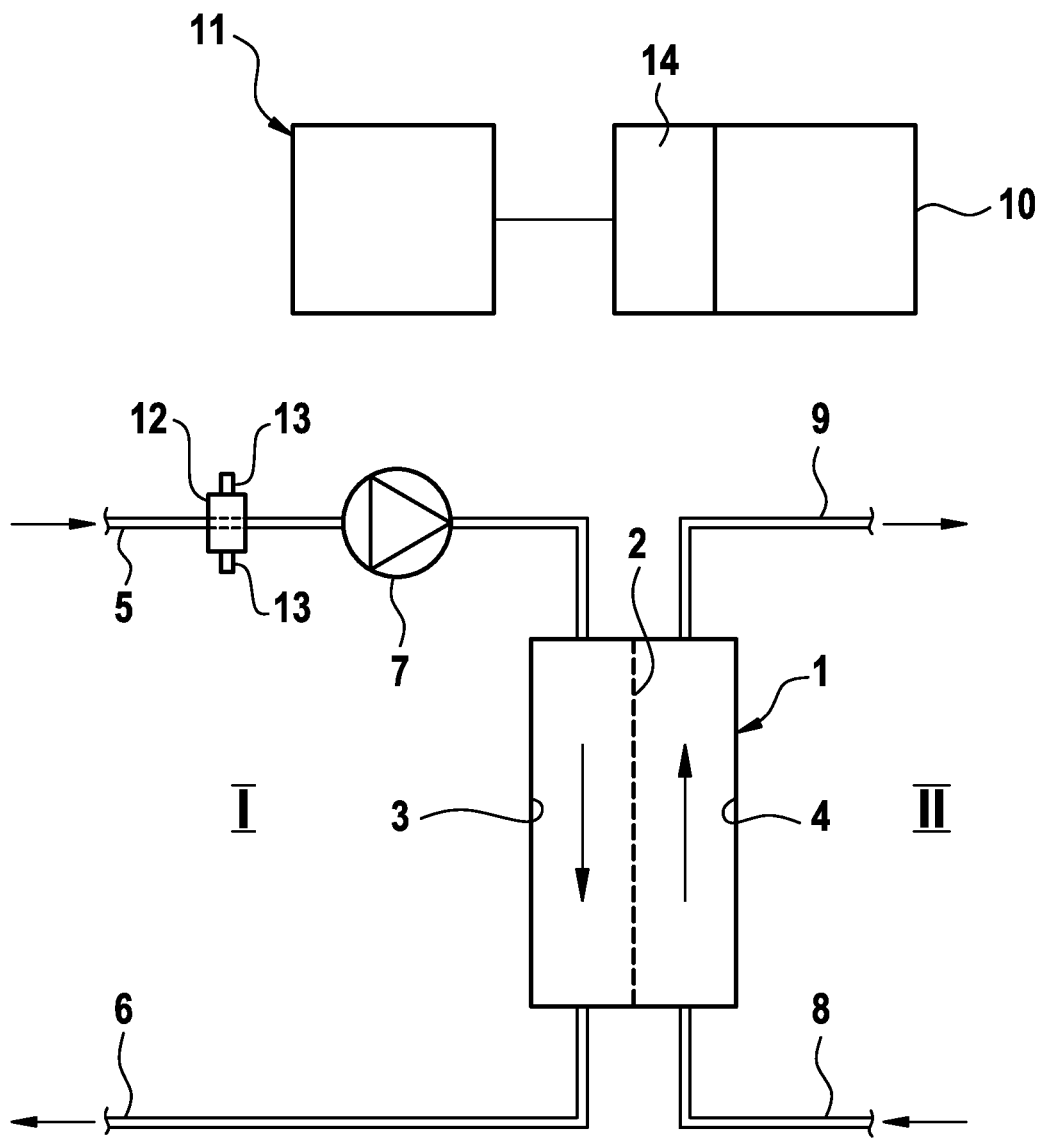
FIG. 1 shows an apparatus for extracorporeal blood treatment together with a device for determining the concentration of a blood constituent in a very simplified schematic representation, according to the present invention.

FIG. 1 shows the components of an apparatus for extracorporeal blood treatment in a very simplified diagrammatic representation. The extracorporeal blood treatment apparatus, for example a dialysis apparatus, comprises a dialyser or filter 1, which is divided by a semipermeable membrane 2 into a blood chamber 3 and a dialysing fluid chamber 4. An arterial blood line 5 leads from the patient to blood chamber 3, whilst a venous blood line 6 leads away from blood chamber 3 and to the patient. A blood pump 7 disposed in arterial blood line 5 conveys the blood in extracorporeal blood circuit I. Dialysing fluid system II of the dialysis apparatus is represented only in outline. It comprises a dialysing fluid supply line 8 leading to dialysing fluid chamber 4 and a dialysing fluid discharge line 9 leading away from dialysing fluid chamber 4. Arterial and venous blood lines 5, 6 are hose lines which are at least partially permeable to light. Furthermore, the blood treatment apparatus comprises a central control unit 10, with which the individual components, for example blood pump 7, are controlled.

Device 11 for determining the concentration of specific blood constituents in a patient's blood can be a component part of the extracorporeal blood treatment apparatus or form a separate component. When device 11 is a component part of the blood treatment apparatus, it can make use of components which are in any case present in the blood treatment apparatus.

Device 11 for determining the concentration of blood constituents, in particular the haemoglobin concentration (Hb), the haematocrit (Hkt) or the relative blood volume (RBV), comprises a clamping unit 12, represented only in outline in FIG. 1, for receiving the hose line, in particular arterial blood line 5, and a measurement unit 13 for coupling light into the blood flowing through blood line 5 and measuring the light emerging from the blood. Measurement unit 13 cooperates with a computing and evaluation unit 14, which determines the concentration of the blood constituent from the measured values. A detailed description of the evaluation of the measured values for determining the blood constituents will be dispensed with, since the determination of the concentration of the blood constituent from the measured values is known. The determination of the blood constituents is described in detail for example in European Patent No. EP 1 579 196 B1.

In the present exemplary embodiment, computing and evaluation unit 14 for determining the concentration of a blood constituent is a component part of central control unit 10 or the computing and evaluation unit of the extracorporeal blood treatment apparatus. Separate units can however also be provided.

Figure 2:
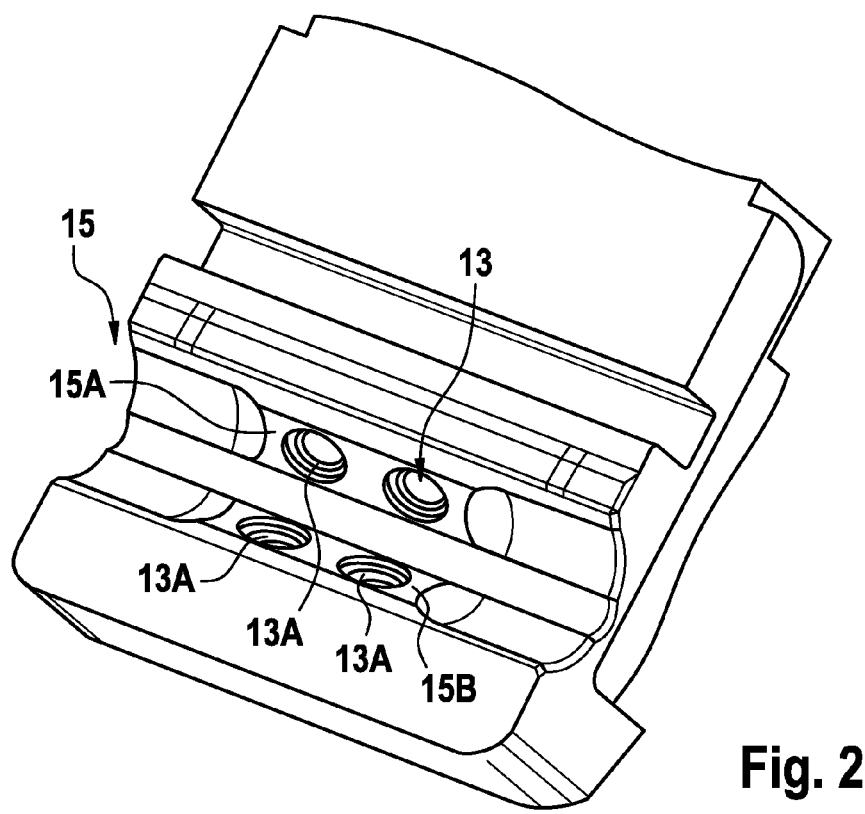
FIG. 2 shows the one receiving element of the clamping unit of the device for determining the concentration of a blood constituent in a perspective representation, according to the present invention.
Figure 3:
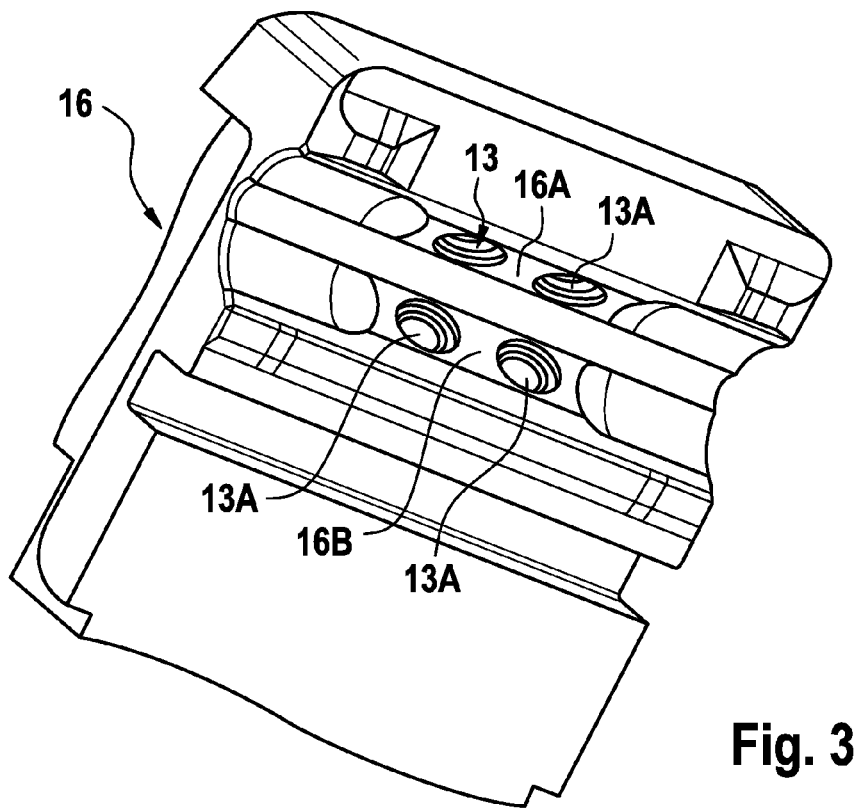
FIG. 3 shows the other receiving element of the clamping unit in a perspective representation, according to the present invention.

FIGS. 2 and 3 show receiving elements 15, 16 of clamping unit 12 together with measurement unit 13 of device 11 for determining the blood parameters.

Clamping unit 12 comprises two receiving elements 15, 16, between which round hose line is clamped, so that the hose line acquires a square cross-section. For the insertion of the hose line, receiving elements 15, 16 can be moved towards one another along an axis a. An electric motor-driven actuation mechanism, which is not represented in FIGS. 2 and 3, is used to move clamping elements 15, 16 from a position releasing the hose line into a position clamping the hose line.

Receiving elements 15, 16 each comprise two plane contact faces 15A, 15B and 16A, 16B respectively, which in each case form a right angle. The axis on which receiving elements 15, 16 are moved forms an angle of 45° with plane contact faces 15A, 15B and 16A, 16B respectively.

Measurement unit 13 comprises a plurality of light emitters and light detectors 13A which are disposed around the periphery of the hose line. The plane contact faces of the receiving elements comprise corresponding light outlet and inlet openings. Light emitters and light detectors 13A are light-emitting diodes (LEDs).

The electromotive drive and the actuation mechanism of the clamping unit are described in detail below.

Clamping unit 12 comprises two receiving elements 15 and 16 described by reference to FIGS. 2 and 3 which, in order to clamp the hose line, are moved towards one another out of a position releasing the hose line into a position clamping the hose line by applying a predetermined clamping force. In order to tension the receiving elements, an actuation mechanism 17 is provided which is driven by an electromotive drive 43.

Actuation mechanism 17 comprises a first pair of lever arms 18, 19, which are disposed on the one side of the two receiving elements 15, 16, and a second pair of lever arms which are disposed on the other side of receiving elements 15, 16.

Figure 4:
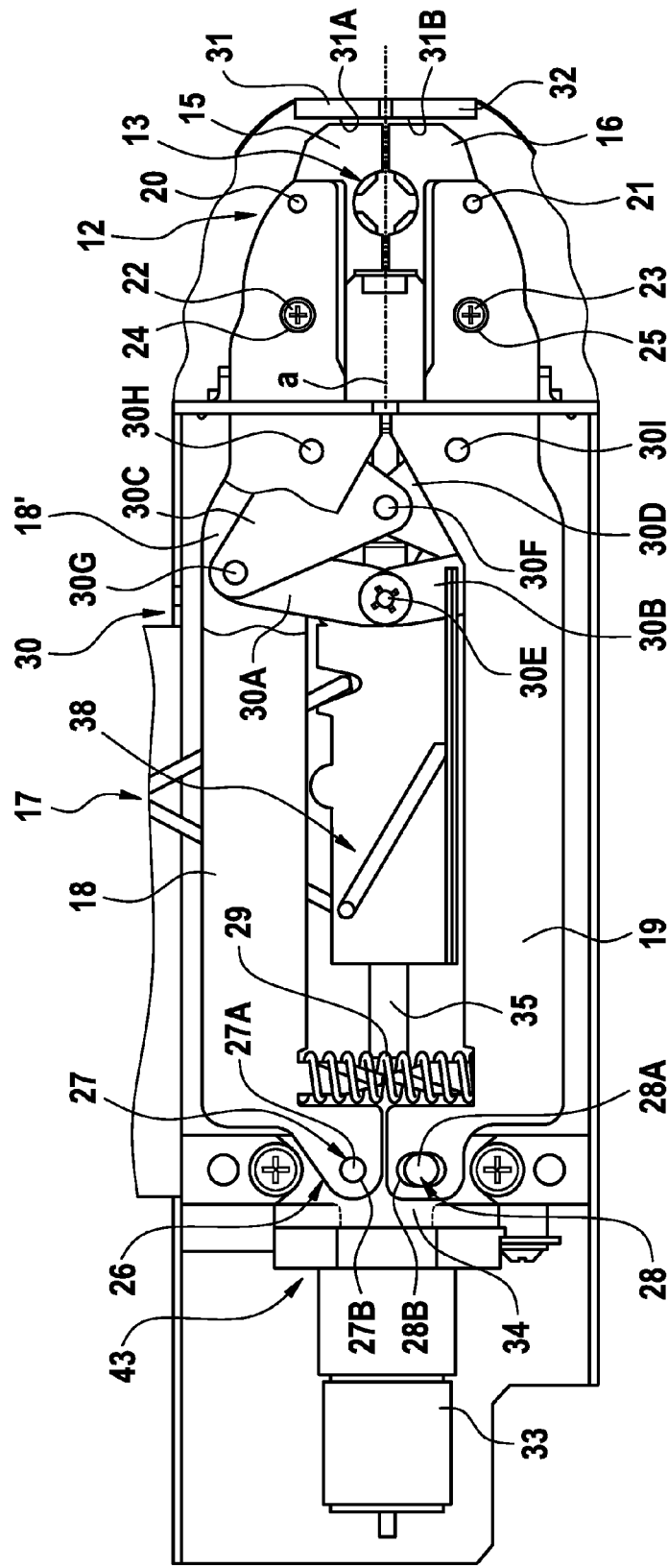
FIG. 4 shows a simplified representation of the electromotive drive and the actuation mechanism of the device for clamping the hose line, according to the present invention.

In the situation represented in FIG. 4, the one lever arm is denoted as upper lever arm 18 and the other lever arm as lower lever arm 19, lever arms 18, 19 lying on the one side of the receiving elements being denoted as the front lever arms and the lever arms lying on the other side as the rear lever arms. Upper front lever arm 18 is represented by a broken line in FIG. 4, so that rear upper lever arm 18' can be seen. Since the structure is symmetrical, only the part of actuation mechanism 17 comprising front lever arm 18, 19 is described. The part of the actuation mechanism for the rear lever arm pair is identical to that of the front lever arm pair.

Receiving elements 15 and 16 are mounted in a pendulum-like manner on the front end pieces of lever arms 18, 19. The bearing point for upper receiving element 15 is denoted by 20 and the bearing point for lower receiving element 16 is denoted by 21. The bearing can take place by means of pins (not represented), which sit in holes of receiving elements 15, 16 and lever arms 18, 19.

To limit the pendulum-like motion, use is made of pins 22, 23, which extend out of receiving elements 15, 16 into holes 24, 25 of lever arms 18, 19, which are disposed laterally beside bearing points 20, 21 and have a larger internal diameter than the external diameter of pins 22, 23. The upper and lower regions of holes 24, 25 therefore form stops, with which the pendulum-like movements of receiving elements 15, 16 are limited. The receiving elements can thus perform only slight tilting movements.

Whereas receiving elements 15, 16 are mounted in a pendulum-like manner on the front end pieces of the two lever arm pairs, the rear end pieces of the lever arm pairs are mounted in a rotational manner on a part of housing 26 of the clamping unit. The upper bearing point of upper lever arm 18 is denoted by 27 and the lower bearing point of lower lever arm 19 is denoted by 28. Upper bearing point 27 is formed by a pin 27A of housing part 26, which sits in a hole 27B in the rear end piece of upper lever arm 18. Lower bearing point 28 is formed by a pin 28A, which has a larger diameter than pin 27A of upper bearing point 27 and sits in an oblong hole 28B on the rear end piece of lower lever arm 19. Oblong hole 28B of lower lever arm 19 extends normal to the longitudinal direction of lever arms 18, 19. Lower lever arm 19 can therefore perform a slight tilting movement upwards or downwards.

Lower lever arm 19 is pre-tensioned in a spring-loaded manner by a pressure spring 29 disposed between upper and lower lever arm 18, 19 in the region of their end pieces in a position in which lower pin 28A strikes against the upper part of oblong hole 28B. In this position, lower lever arm 19 is positioned slightly inclined, the upper end piece of lever arm 19 pointing slightly upwards. This position in which receiving elements 15, 16 are opened is not represented in FIG. 4. The closed position is shown in FIG. 4.

The two receiving elements 15, 16 are moved towards one another or away from one another by the fact that lever arms 18, 19 are swivelled upwards or downwards by a toggle system 30, which engages at the two bearing points 27, 28. Toggle system 30 is actuated by electromotive drive 43.

Toggle system 30 will next be described in detail. Toggle system 30 comprises a first pair of levers 30A and 30B and a second pair of levers 30C and 30D. First lever pair 30A, 30B comprises an upper and a lower lever 30A and 30B, respectively, whilst the second lever pair comprises an upper and a lower lever 30C and 30D, respectively.

The inner ends of levers 30A, 30B of the first lever pair are connected to one another in an articulated manner at an inner articulation point 30E, whilst the inner ends of levers 30C, 30D of the second lever pair are connected to one another in an articulated manner at an inner articulation point 30F. The outer ends of levers 30A to 30D of the two lever pairs are connected to one another in an articulated manner at articulation points 30G.

Levers 30C, 30D of the second lever pair are constituted as triangular straps, which are connected in an articulated manner to upper and lower lever arms 18, 19 at articulation points 30H, 30I disposed laterally offset with respect to articulation points 30G.

When articulation points 30H, 30I are moved towards one another or away from one another in a direction running normal to the longitudinal axis of lever arms 18, 19, the lever arms are swivelled about bearing points 27, 28, so that receiving elements 15, 16 open or close.

Receiving elements 15, 16 mounted in a pendulum-like manner are aligned against one another by guide elements 31, 32 during the opening and closing. Guide elements 31, 32 comprise guide faces 31A, 31B, which engage at the front faces of the receiving elements. Guide faces 31A, 31B of guide elements 31, 32 lie in a plane which extends normal to longitudinal axis a of the clamping unit. Guide elements 31, 32 are represented solely in outline in FIG. 4.

When toggle system 30 is actuated, levers 30C, 30D of the second lever pair are swivelled in such a way that articulation points 30H, 30I are moved towards one another or away from one another. Receiving elements 15, 16 are thus closed or opened.

Electromotive drive 43 for actuating toggle system 30 is described in detail below.

Figure 5A:
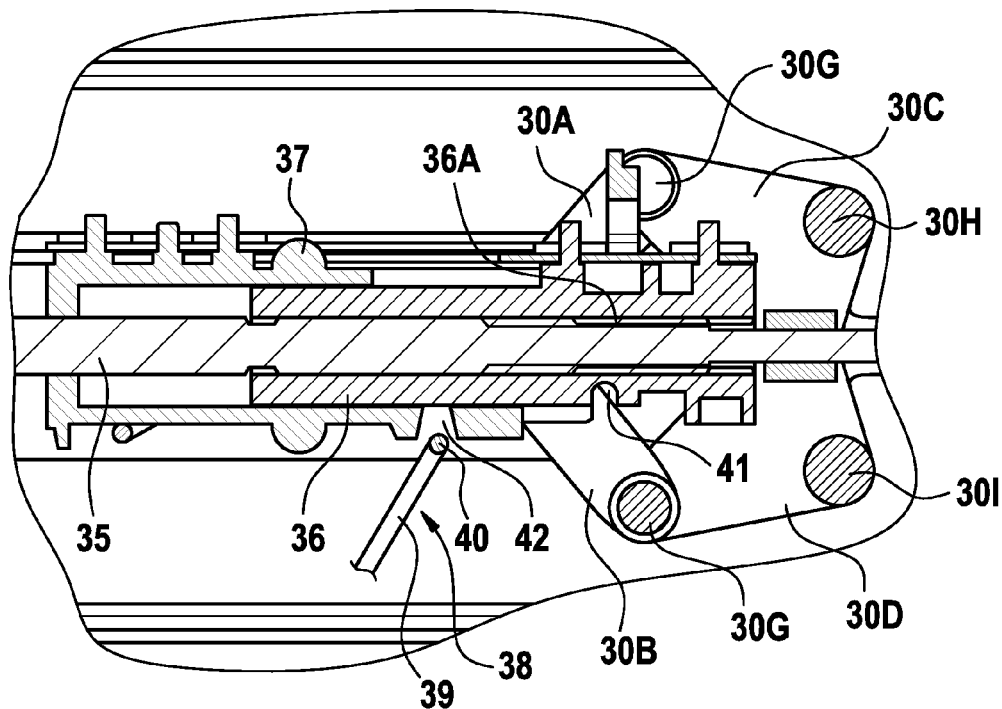
FIG. 5A shows a partial view of the electromotive drive and the actuation mechanism in the position releasing the hose line, according to the present invention.
Figure 5B:
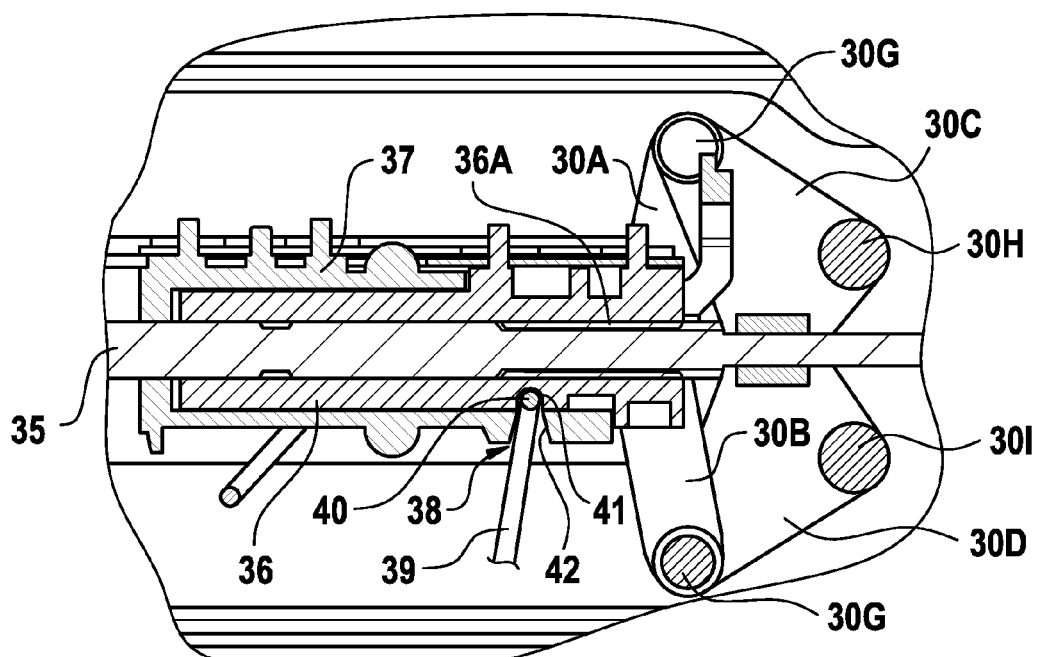
FIG. 5B shows a partial view of the electromotive drive and the actuation mechanism in the position clamping the hose line, according to the present invention.

Electromotive drive 43 comprises an electric motor 33 with a spindle drive 34. Spindle 35 of spindle drive 34 extends in the longitudinal direction of the clamping unit between the two lever arm pairs. A driver 36, which is constituted as a hollow-cylindrical body and which has an internal thread 36A, sits on spindle 35 (FIGS. 5A, 5B). By rotating spindle 35 with electric motor 33, driver 36 is pushed back and forth in the direction of the longitudinal axis of the clamping unit.

FIGS. 5A and 5B show in a partially cut-away representation a part of actuation mechanism 17 and electromotive drive 43 when receiving elements 15, 16 are opened (FIG. 5A) and when the receiving elements are closed (FIG. 5B). FIGS. 5A and 5B show that hollow-cylindrical driver 36 sits in the bore of an actuation element 37, which is also constituted as a hollow-cylindrical body. When actuation element 37 and driver 36 are not locked together, actuation element 37 can be displaced manually in the longitudinal direction of the clamping unit. However, when the driver and the actuation element are locked, the driver can drive the actuation element by rotating spindle 35, so that actuation element 37 is pushed back and forth. The front end of actuation element 37 is connected in an articulated manner to the inner ends of levers 30A, 30B of the first lever pair. Toggle system 30 is thus actuated by rotating spindle 35 with electric motor 33.

FIG. 5A shows the position of the lever of toggle system 30, in which receiving elements 15, 16 are opened. In this position, the two bearing points 30H, 30I, at which levers 30C, 30D of the second lever pair of toggle system 30 are connected to lever arms 18, 19, are spaced farthest apart.

When actuation element 37 is pushed forward, toggle system 30 causes receiving elements 15, 16 to move towards one another, so that a predetermined clamping force is exerted on the hose line (FIG. 5B). When the receiving elements are compressed by toggle system 30, lower lever arm 19 mounted in a slightly pendulum-like manner at lower bearing point 28 exerts a slight tipping motion downwards against the pre-tensioning force of pressure spring 29, so that pin 28A comes to rest in the middle between the lateral limits of oblong hole 28B (FIG. 4). In this position, the clamping force applied by the receiving elements on the hose line is kept within a defined range, which results from the leverage conditions arising here and the spring force of pre-tensioned pressure spring 29. Influences of manufacturing tolerances or changing ambient conditions, for example temperature changes or ageing of the material, are thus compensated for, so that reproducible measurement results can be achieved. Since the lever arms of the two lever pairs can be moved independently of one another and the receiving elements are held on both sides, a uniform introduction of the forces to the receiving elements takes place.

Receiving elements 15, 16 can be opened by the fact that driver 36 of spindle drive 34 can be moved back from the front to the rear position by rotating spindle 35. The two bearing points 30H, 30I of toggle system 30 are thus moved away from one another (FIG. 5A).

For the manual opening of receiving elements 15, 16, the clamping unit comprises an unlocking mechanism 38, which will be described in detail below.

Unlocking mechanism 38 also permits opening of the receiving elements if electromotive drive 43 should fail on account of a malfunction. Unlocking mechanism 38 comprises an unlocking element 39, which connects driver 37 and actuation element 38 fixedly together in the locked position (FIG. 5B). Consequently, the actuation element is then driven by the driver.

Unlocking element 39 is constituted in the manner of a swivellable lever arm. Located at one end of arm 39 is a locking pin 40, with which actuation element 37 and driver 36 are locked together. In the locked position, locking pin 40 engages, through a slot-shaped cutout 41 in actuation element 37 running normal to the longitudinal axis, in a groove 42 in driver 36 running normal to the longitudinal axis, wherein the unlocking element rests on a flank of slot-shaped cutout 41, so that driver 36 drives actuation element 37 when receiving elements 15, 16 are closed.

For the purpose of unlocking, unlocking element 39 is swivelled about an axis running normal to the longitudinal axis of the driver and the actuation element, so that locking pin 40 releases actuation element 37. Receiving elements 15, 16 can now be opened manually in order that the hose line can be removed.

The actuation of unlocking element 39 can be carried out manually or by a further actuation mechanism, which however is not represented in the figures. This actuation mechanism can be an electromotive or pneumatic actuation mechanism, which swivels the unlocking element in order to open the receiving elements.

What is claimed is:

1. A device for clamping a hose line for determining a concentration of a constituent of blood in a hose line of an extracorporeal blood circuit of an extracorporeal blood treatment apparatus, comprising:
    a clamping unit which comprises first and second receiving elements for clamping the hose line;
    a measurement unit for coupling electromagnetic radiation through the hose line into the blood and measuring the electromagnetic radiation emerging through the hose line from the blood,
    wherein the clamping unit comprises an actuation mechanism and an electromotive drive for the actuation mechanism, wherein the actuation mechanism is constituted such that, when a clamping force is applied, the first and second receiving elements move from a position releasing the hose line into a position clamping the hose line, and
    wherein the clamping unit comprises an unlocking mechanism, which is constituted such that, by actuating an unlocking element, the actuation mechanism in the position clamping the hose line is decoupled from the electromotive drive, so that the receiving elements can be transferred manually from the position clamping the hose line into the position releasing the hose line.

2. The device according to claim 1, wherein the actuation mechanism comprises a toggle system, wherein the electromotive drive is a spindle drive with a spindle, on which a driver sits which drives an actuation element for the toggle system.

3. The device according to claim 2, wherein the unlocking element connects the driver and the actuation element together in a locked position and releases the actuation element in an unlocked position of the driver.

4. The device according to claim 2, wherein the driver is an essentially hollow-cylindrical body with an internal thread which sits on the spindle of the spindle drive, and the actuation element is an essentially hollow-cylindrical body which sits on the hollow-cylindrical body of the driver in a longitudinally displaceable manner.

5. The device according to claim 4, wherein the essentially hollow-cylindrical body of the actuation element comprises a recess running normal to the longitudinal axis and the essentially hollow-cylindrical body of the driver comprises a groove running normal to the longitudinal axis, wherein the unlocking element comprises a locking pin which, in a locked position, engages in the recess or groove.

6. The device according to claim 5, wherein the unlocking element is fixed in a swivellable manner.

7. The device according to claim 1, wherein the actuation mechanism comprises at least one pair of lever arms, wherein the first receiving element is fixed to one end piece of a first lever arm and the second receiving element is fixed to one end piece of a second lever arm of the at least one pair of lever arms, and an other end piece of the first lever arm is mounted in a rotational manner at a first bearing point and an other end piece of the second lever arm is mounted in a rotational manner at a second bearing point.

8. The device according to claim 7, wherein at least one of the first and second bearing points is constituted such that the other end piece of the second lever arm mounted in a rotational manner at the second bearing point can be displaced between two stops, wherein the other end piece is pre-tensioned in a spring-loaded manner in a direction of a stop.

9. The device according to claim 8, wherein, for the spring-loaded pre-tensioning, at least one pressure spring is provided, which is disposed between the first and second lever arms.

10. The device according to claim 1, wherein a first pair of lever arms and a second pair of lever arms are provided, wherein the first pair of lever arms is disposed on one side of the receiving elements and the second pair of lever arms is disposed on an other side of the receiving elements.

11. The device according to claim 2, wherein the toggle system comprises a first lever and a second lever, which are connected to one another in an articulated manner at one end, and a third lever and a fourth lever, which are connected to one another in an articulated manner at one end, wherein free ends of the first lever and the third lever are connected to one another in an articulated manner and free ends of the second lever and the fourth lever are connected to one another in an articulated manner.

12. The device according to claim 11, wherein the third lever is connected in an articulated manner to a first lever arm and the fourth lever is connected in an articulated manner to a second lever arm of at least one pair of lever arms of the actuation mechanism.

13. The device according to claim 7, wherein the first receiving element is mounted in a pendulum-like manner on the first lever arm and the second receiving element is mounted in a pendulum-like manner on the second lever arm, wherein the pendulum-like motion is limited by stops.

14. The device according to claim 1, wherein guide elements assigned to the receiving elements are provided, said guide elements comprising guide faces engaging with the receiving elements, said guide faces being constituted such that the receiving elements can be moved towards one another and away from one another.

15. The device according to claim 1, wherein the receiving elements each comprise two plane contact faces at right angles to one another, wherein the receiving elements can be moved towards one another in a direction of an axis which forms an angle of 45° with the plane contact faces.

\* \* \* \* \*